(12) United States Patent
Dobler

(10) Patent No.: US 6,251,408 B1
(45) Date of Patent: Jun. 26, 2001

(54) FRAGRANCE SAMPLER INSERT

(75) Inventor: Sven Dobler, New York, NY (US)

(73) Assignee: Orlandi, Inc., Farmingdale, NY (US)

( * ) Notice: Subject to any disclaimer, the term of this patent is extended or adjusted under 35 U.S.C. 154(b) by 0 days.

(21) Appl. No.: 09/531,296

(22) Filed: Mar. 20, 2000

(51) Int. Cl.⁷ .............................. A61K 9/00; B65D 75/26
(52) U.S. Cl. ........................... 424/400; 206/484; 428/905
(58) Field of Search .................. 206/0.5, 484; 424/400; 428/905

(56) References Cited

U.S. PATENT DOCUMENTS

| | | |
|---|---|---|
| 4,487,801 | 12/1984 | Turnbull et al. . |
| 4,493,869 | 1/1985 | Sweeny et al. . |
| 4,606,956 | 8/1986 | Charbonneau et al. . |
| 4,661,388 | 4/1987 | Charbonneau et al. . |
| 4,720,423 | 1/1988 | Fraser . |
| 4,751,934 | 6/1988 | Moir et al. . |
| 4,769,264 | 9/1988 | Dreger . |
| 4,848,378 | 7/1989 | Moir et al. . |
| 5,161,688 | 11/1992 | Muchin . |
| 5,192,380 | 3/1993 | Hanada et al. . |
| 5,391,420 | 2/1995 | Bootman et al. . |
| 5,562,112 | 10/1996 | Gunderman et al. . |
| 5,622,263 | 4/1997 | Greenland . |
| 5,645,161 * | 7/1997 | Whitaker et al. ..................... 206/0.5 |
| 5,666,693 | 9/1997 | Levay . |
| 5,690,130 | 11/1997 | Gunderman et al. . |

* cited by examiner

*Primary Examiner*—Thurman K. Page
*Assistant Examiner*—B. Fubara
(74) *Attorney, Agent, or Firm*—Paul M Denk

(57) ABSTRACT

A fragrance sample is provided which is made from two plies of material. A wall is formed in the bottom ply which defines a well into which a fragrance sample is deposited. The top ply has a wall formed therein which interlocks with the bottom ply wall to cover and close the well. The two plies are then adhered together to form a liquid tight seal between the two plies.

14 Claims, 2 Drawing Sheets

FRAGRANCE SAMPLER INSERT

CROSS-REFERENCE TO RELATED APPLICATIONS

Not Applicable

STATEMENT REGARDING FEDERALLY SPONSORED RESEARCH OR DEVELOPMENT

Not Applicable.

BACKGROUND OF THE INVENTION

This invention relates to fragrance samplers which are inserted in magazines or used in direct mailings.

Traditionally fragrance samplers were dry pre-scented blotter cards that had to be individually overwrapped to contain the fragrance for use in direct mail or magazine advertising. Beginning in the late 1970's, the micro-encapsulated Scentstrip® style magazine and direct mail insert was introduced. The Scentstrip insert is described in U.S. Pat. No. 5,093,182 to Ross. This product was produced on wide web offset printing equipment and therefore offered significant cost efficiencies for mass marketing. However, this was still a dry sample since the water moisture in the deposited fragrance slurry would very quickly wick into the paper substrate and leave the product sample dry. In fact, the entire technology depended on this moisture wicking since the wet microcapsules would not bond to the paper and would not break upon opening of the sampler. The microcapsules only break and release the fragrance oil when they are dry and are bonded to the paper. The draw back with this product was that it did not replicate the actual wet perfume product very well. In order to sample the fragrances in its real life wet form, the moisture wicking of the wet fragrance slurry deposited in the wide web offset printing process needed to be prevented. This was most easily accomplished by using existing narrow web flexographic label printing technology to create a pressure sensitive product that incorporated a wet fragrance or cosmetic sample material between impervious barrier materials such as plastic films and foil structures.

Currently there are three main fragrance sampler patents that guide us in wet fragrance or cosmetic sampling in magazines and direct mail. One is U.S. Pat. No. 5,391,420 to Bootman, which describes a pressure sensitive label comprising two plies of a film or plastic material: one bottom pressure sensitive ply, a deposit of fragrance material and an overlay of a second ply which traps said fragrance deposit. The sealing is by heat seal. The draw back of this product is that the fragrance material is often forced into and through the seal areas under pressure from the stacking forces of many magazines or inserts in distribution.

The other patent is U.S. Pat. No. 5,161,688 to Muchin which perfects upon the Bootman product by introducing a center ply material which has a die-cut window. This window ply is introduced onto the bottom pressure sensitive ply and thus creates a well for the fragrance material. The top, third ply is then added and the result is that stacking forces are distributed on to the widow ply and the fragrance material is exposed to less forces that may lead to seal failures and leakage: a major defect in the original product. A modification of this second patent concept is described in U.S. Pat. No. 5,622,263 to Greenland. Greenland uses a liquid polyethylene or other hot liquid plastic material that creates the above-mentioned well and also assists in the heat sealing process. The draw back of the Muchin patent is that the additional window ply involves additional cost and manufacturing complications for die-cutting and introducing the third ply in the process. The Greenland concept also adds additional material cost and slows the process as the liquid plastic material needs to be deposited and bonded to the top and bottom ply. Further, the hot liquid plastic material introduces foreign odor and can, in some circumstances, contaminate the cosmetic or fragrance sampling material.

BRIEF SUMMARY OF THE INVENTION

The current invention creates a protective well for the cosmetic or fragrance material without the cost or slowdown of the additional third window ply of film or liquid polyethylene barrier wall deposit. The well is created by embossing, debossing or both embossing and debossing an interlocking double well wall into the two foil ply materials, thus creating a structure that is significantly stronger and can withstand stack pressure and forces experienced during distribution and mailing. The cosmetic or fragrance sampling material is deposited into the well. The top and bottom plies are bonded by a cohesive bond, by adhesive, or by heat seal bonding. Under stacking pressure in magazines, such described samples will maintain the seals better than the Bootman product and will be more cost effective than the Greenland or Muchin products.

BRIEF DESCRIPTION OF THE SEVERAL VIEWS OF THE DRAWINGS

Corresponding reference numerals will be used throughout the several figures of the drawings.

DETAILED DESCRIPTION OF THE INVENTION

Figure 1:
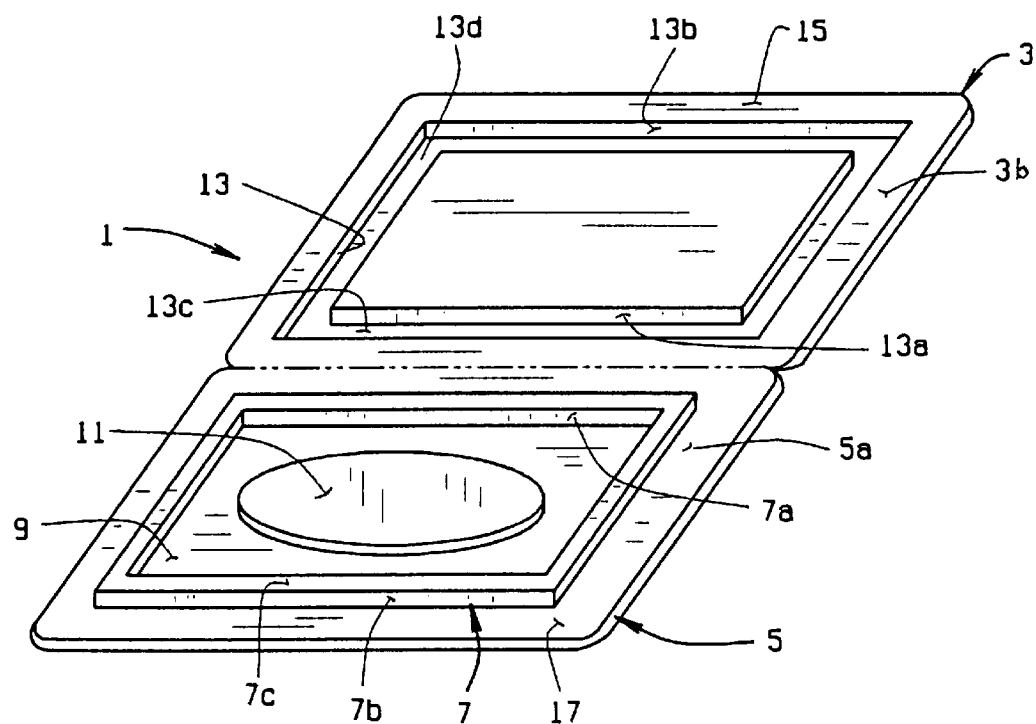
FIG. 1 is a perspective view of a fragrance sampler of the present invention prior to assembly of the sampler.

The following detailed description illustrates the invention by way of example and not by way of limitation. This description will clearly enable one skilled in the art to make and use the invention, and describes several embodiments, adaptations, variations, alternatives and uses of the invention, including what I presently believe is the best mode of carrying out the invention.

A sampler 1 of the present invention includes a top ply 3 and a bottom ply 5, both of which are preferably foil. The plies can alternatively be made of an acetate or other paper and plastic film laminated or non laminated barrier plies.

The top and bottom plies 3 and 5 each include top and bottom surfaces 3a, 5a and 3b, 5b. A wall 7 is formed in the bottom ply 5 which extends up from the bottom ply's upper surface 5a. The wall 7 has an inner surface 7a, an outer surface 7b, and a top surface 7c which define a channel 7d in the bottom ply bottom surface 5b. The channel 7d is preferably rectangular in cross-section, and the wall 7 defines a "double wall." The wall 7 also defines a well 9 into which a wet fragrance sample 11 can be deposited.

Figure 2:
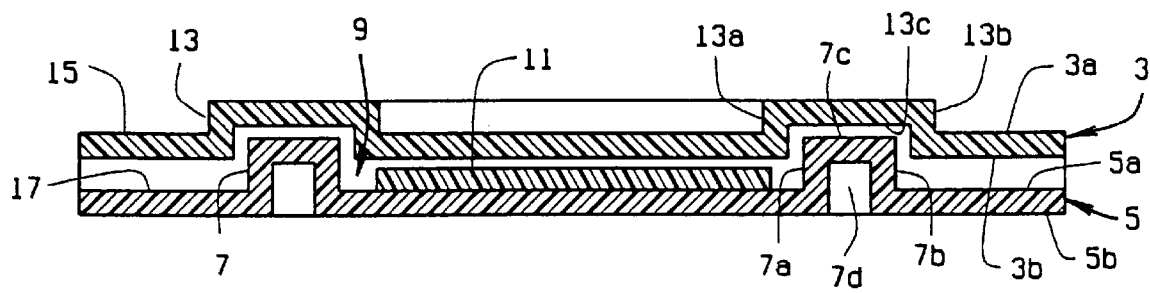
FIG. 2 is a cross-sectional view of the sampler when assembled.

An opposing wall 13 is formed in the top ply 3 and extends upwardly from the top ply bottom surface 3b (with reference to FIG. 2. The wall 13 has an inner surface 13a, an outer surface 13b, and a bottom surface 13c which, in combination, define a channel 13d in the top ply top surface 3a. As with the bottom ply channel 7d, the channel 13d is preferably rectangular in cross-section, and the wail 13 is a "double wall." As seen in FIG. 2, the wall 13 in the upper ply has dimensions slightly larger than the dimensions of the bottom ply wall 7, and the channel 13*d* is slightly wider than the channel 7*d*. Thus, the top ply wall 13 receives the bottom ply wall 7, as seen in FIG. 2, so that the walls 7*a–c* defining the lower ply channel 7*d* are substantially adjacent the walls 13*a–c* defining the upper ply channel 13*d*.

The walls 7 and 13 are preferably formed by an embossing/debossing process.

As can be seen in FIGS. 1 and 2, when the walls 7 and 13 are formed, the top and bottom plies each include a frame 15, 17 surrounding the walls 7 and 13, respectively. The top ply 3 and bottom ply 5 are adhered together to cover and close the well 9 so that the sample 11 will be sealed in the well 9 between the two plies. The plies can be joined by heat sealing the two plies together or using an adhesive to bond the top plies together. If an adhesive is used, the adhesive can be cationic cure coating adhesive, or other equally acceptable adhesive which will form a liquid tight barrier to prevent premature release of the fragrance contained in the well 9.

Figure 3:
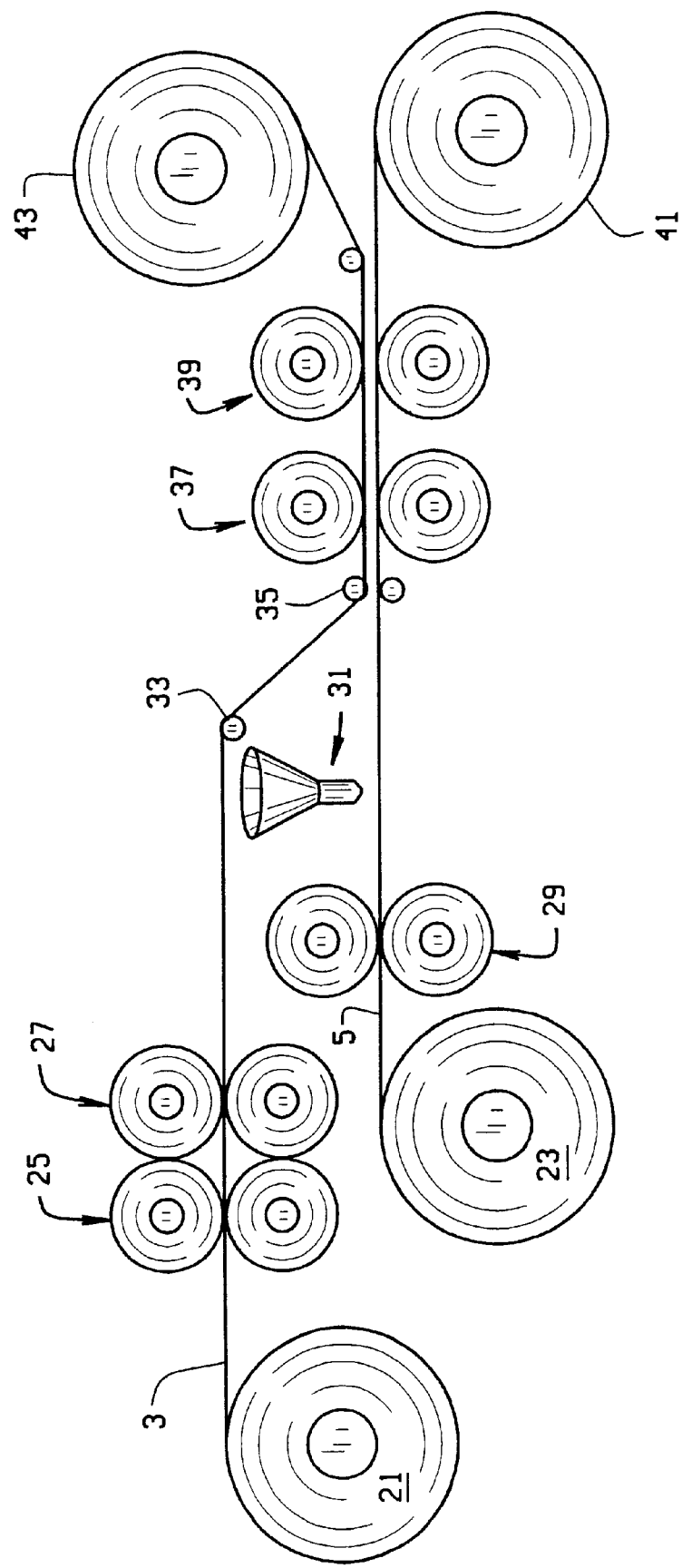
FIG. 3 is a schematic drawing of the sampler producing process.

The process for producing the sampler 1 is shown schematically in FIG. 3. Webs of the top and bottom ply material are originally contained on rollers 21 and 23, respectively. The top ply material is pulled off the top ply roller 21 and passed through a printer station 25 and then through an embossing station 27. At the printer station 25 desired graphics are printed on the top surface 3*a* of the top ply 3. The top ply wall 13 is formed at the embossing station 27. The top foil laminated ply is printed on a narrow web flexographic printing press such as a Hunkeler press, with all subsequent finishing steps performed in-line.

While the top ply is being processed, the bottom ply material is pulled off the bottom ply roller 23 and passed through an embossing station 29 where the bottom ply wall 7 is formed. A rotary embossing tool is used to push up or emboss the wall 7 on the bottom ply to form the well 9. The bottom ply embossing can be also be formed by intermittent flat bed embossing methods.

The bottom ply 5 is passed under an injection station 31 where a liquid fragrance sample is deposited in the wall 9. The sample 9 can be deposited in any other desired manner, such as extrusion, flexographic equipment or silkscreen.

After the top ply has been printed and after the wall 13 is formed in the top ply, the top ply is passed about a pair of rollers 33 and 35 to bring the top ply 3 into close proximity with the bottom ply 5. The path of travel of the bottom ply is preferably substantially horizontal, at least after the fragrance sample has been deposited in the bottom ply well 9, to avoid spilling of the sample. Thus, the top ply 3 is preferably brought to the bottom ply 5. However, the process could be designed so that the bottom ply 5 is brought up to the top ply 5. The two plies are then passed through a sealing station 37 where the two plies are adhered together to form a liquid tight seal which will contain the fragrance sample in the chamber 9. The sealing station interlocks with the raised well wall 7 with the top ply wall 13 to form a safe, closed well for the sample material 9. As can be appreciated, the webs of top ply and bottom ply material move at an indexed rate such that when the two plies are brought together at the sealing station, the top ply wall 13 will be in alignment with the bottom ply wall 7. The sealing station 37 is preferably is a heat sealer, and the top and bottom plies can be adhered or sealed together for example, by ultrasonic welding, or other standard heat sealing processes which will create a seal between the two plies. Alternatively, as noted above, the sealing station can utilize an adhesive, such as cationic cure coating adhesives, traditional cohesive seals, or adhesive seals, which will bind the top and bottom plies together to form the seal.

The joined plies are then passed to a die-cut station 39 where side portions of the frames 15 and 17 are removed from the formed samplers. The die-cutting step can be performed with either rotary or flat bed equipment. The formed samplers are then collected on a product roller 41. Product is delivered in roll form for automatic applications to other printed materials. The waste material can be collected on a waste roller 43.

As can be appreciated, the sampler 1 of the present invention is easily formed from only two plies of material. The walls 7 and 13 are substantially adjacent each other, and effectively form four walls (7*a*, 7*b*, 13*a*, and 13*b*), which are separated by the wall sections 7*c* and 13*c*. The walls 7 and 13 will thus carry the stacking or compression forces to reduce seal failures and fragrance leaks.

As various changes could be made in the above constructions without departing from the scope of the invention, it is intended that all matter contained in the above description or shown in the accompanying drawings shall be interpreted as illustrative and not in a limiting sense. For example, the top and or bottom plies may be alternatively embossed or debossed to create single walls versus interlocking double walls. Additionally, the top ply wall can be sized to surround the bottom ply wall, i.e., the bottom ply outer wall 7*b* would be adjacent the top ply inner wall 13*d*. In this instance, instead of both walls extending upwardly through the top surfaces of the two plies, the wall 13 would extend down from the bottom 3*b* of the top ply. These examples are merely illustrative.

What is claimed is:

1. A fragrance sampler for inserting into a magazine or mass mailing, the sampler including:
   a bottom ply having an upper surface and a lower surface, and a wall formed in the upper surface defining a well;
   a fragrance sample in the well; and
   a top ply having an upper surface and a lower surface and a wall formed in the top ply upper surface; the top ply wall defining a channel in the lower surface of the top ply; the top ply channel and the bottom ply wall being sized such that the bottom ply wall is received in the top ply channel; the top ply and bottom ply being adhered together to form a seal to substantially prevent leakage of the fragrance sample.

2. The fragrance sampler of claim 1 wherein the top and bottom ply walls are formed by embossing or debossing process.

3. The fragrance sampler of claim 1 wherein the top and bottom plies are adhered together in a heat sealing process.

4. The fragrance sampler of claim 1 wherein the top and bottom plies are adhered together by a cationic cure coating adhesive.

5. The fragrance sampler of claim 1 wherein the walls of at least one of the upper and lower plies defines a double wall.

6. A method of forming a fragrance sampler for insertion in a magazine, the method comprising:
   (a) pulling top ply webbing from a top ply roller;
   (b) forming a channel in the top ply webbing;
   (c) pulling bottom ply webbing from a bottom ply roller;
   (d) forming a wall in the bottom ply webbing, the wall defining a well;

(e) depositing a fragrance sample in well;

(f) bringing the top and bottom plies together, such that the bottom ply wall is received in the top ply channel;

(g) adhering the top and bottom plies together to form a seal between the top and bottom plies which will substantially prevent leakage of the fragrance sample from the sampler.

7. The method of claim 6 wherein the steps of forming the channel in the top ply and the wall in the bottom ply includes embossing or debossing the walls in the plies.

8. The method of claim 6 wherein at least one of the bottom ply wall are double walled.

9. The method of claim 6 wherein the step of depositing the fragrance sample in the well includes one of injection depositing of the sample, extrusion of the sample, flexographic printing of the sample, or silkscreen printing of the sample.

10. The method of claim 6 including step of die-cutting waste material from the samplers and collecting formed samplers on a product roll.

11. The fragrance sampler of claim 1 wherein the fragrance sample may include one of a cosmetic creme, lotion, hair color tint, or other cosmetic ingredient.

12. The method of claim 6 wherein a pressure sensitive material with release liner is used as the bottom ply so as to result in a product that can later be readily applied to another substrate using affixing equipment.

13. The method of claim 6 wherein a pressure sensitive adhesive is applied to the bottom layer ply after the embossing process and a release liner is added so as to result in a pressure sensitive label product that can later be readily applied to another substrate using automatic affixing equipment.

14. The method of claim 6 wherein a third, pressure sensitive ply with release liner is adhered to the bottom ply after the embossing process, thus allowing automatic affixing to another substrate and also allowing for the complete removal of the two-ply pouch from the substrate to which it was affixed.

* * * * *